United States Patent [19]

Adair

[11] Patent Number: 5,488,875
[45] Date of Patent: Feb. 6, 1996

[54] EMISSIONS TESTING EQUIPMENT SUPPORT

[76] Inventor: Bob A. Adair, 1990 Coal Creek Rd., Longview, Wash. 98632

[21] Appl. No.: 298,352

[22] Filed: Aug. 29, 1994

Related U.S. Application Data

[63] Continuation of Ser. No. 859,196, Mar. 27, 1992, abandoned.

[51] Int. Cl.$^6$ ................................................. G01N 1/26
[52] U.S. Cl. ................................... 73/863.82; 73/863.81
[58] Field of Search ........................... 73/863.82, 863.81, 73/866.5, 863.83, 863.84, 863.85

[56] References Cited

U.S. PATENT DOCUMENTS 3,888,123  6/1975  Künteiger et al. .................. 73/863.85
3,998,102 12/1976  Santorilla ............................. 73/863.82
4,817,293  4/1989  Daverio et al. ...................... 73/863.85
4,942,772  7/1990  Welker ................................. 73/863.83

*Primary Examiner*—Hezron E. Williams
*Assistant Examiner*—Nashmiya Ashraf
*Attorney, Agent, or Firm*—Klarquist Sparkman Campbell Leigh & Whinston

[57] ABSTRACT

An emissions testing equipment support includes a probe carrier movable on a walkway and which carries an emissions sampling probe supported for movement along a probe guide for insertion into and removal from a monitoring port. The elevation of the probe guide is adjustable to permit raising and lowering of the probe to align the probe with the monitoring port. In one embodiment, the probe carrier is an upright rack having inverted u-shaped end sections which carry a probe guide rail and an emissions sample support tray.

22 Claims, 3 Drawing Sheets

EMISSIONS TESTING EQUIPMENT SUPPORT

This application is a continuation, of application Ser. No. 07/859,196, filed on Mar. 27, 1992, now abandoned.

BACKGROUND OF THE INVENTION

The present invention relates to the testing of emissions from a chimney or stack at an industrial or manufacturing plant and more specifically to the support of an elongated sampling probe for insertion into monitoring ports of the stack for obtaining emissions samples for analysis.

From an environmental standpoint, it is desirable to monitor emissions in industrial stacks for purposes of determining the air pollution properties of such emissions. By monitoring these gases, one may also obtain an indication that parameters of plant operation need adjustment to reduce or vary the content of the emissions. In addition, governmental regulations requiring the monitoring of stack emissions have become more rigorous over time.

With reference to the prior art device of FIG. 1, a stack 10 is shown with plural stack gas monitoring ports 12, 14, located ninety degrees apart about the circumference of the stack. Conventional air pollution monitoring requires the insertion of an elongated emissions sampling probe 16 that will reach substantially all the way across the diameter of the stack, typically anywhere from six feet to fifteen feet. During testing, the stack gases are normally sampled at several locations across the stack diameter. As shown in FIG. 1, a bracket 20 is mounted to the stack 10 at a location above the monitoring port 12. A guide rail 22 has an inner end 24 connected to the bracket 20 and its outer end 26 supported by a chain 28 which in turn is connected to the stack 10. The emissions sampling probe 16 is coupled to emissions monitoring equipment 30, 31. The equipment 30, 31, by way of an umbilical tube, a portion of which is indicated at 32, is coupled to a control area. The equipment 30 is suspended by a support bracket 34 from the guide 22. Rollers, not shown, at the upper end of bracket 34 roll along a track defined by the guide 22 to permit insertion and withdrawal of the probe 16 from the monitoring port 12. Typically, a base or walkway 40, which may be a section of the roof of a building, provides a place for emissions testing personnel to stand and gain access to the monitoring ports 12, 14 during emissions testing.

Following the emissions testing at port 12, the guide rail 22 is disconnected from bracket 20 and the chain 28 is also disconnected. The rail 22, bracket 34, equipment 30 and probe 16 are then moved to the next monitoring port, such as the port 14. The rail 22 is then connected to a bracket 42 above the port 14 and another chain 44 is coupled to the outer end 26 of the rail 22. As a result, the assembly is positioned at the desired location for insertion of the probe 16 into the port 14.

In general, the movement of the test equipment and probe between the ports is a very time consuming and difficult process. It is not unusual for the equipment hanging from the rail 22 to weigh between 40 and 80 pounds, a weight which is difficult and cumbersome to handle, especially when personnel are working above their heads to lift this weight. In addition, it is difficult to physically move the equipment between ports without disturbing the seal of each piece of equipment during the move. Also, following insertion into a port, the probe 16 frequently becomes very hot, for example 250° F. or more. This makes it difficult to handle the probe during movement of the probe between locations. Also, containers of gas samples obtained from the testing equipment are often stored in ice water baths which rest on the walkway, giving rise to the possible spilling of the ice water on the personnel during the equipment movement. During typical stack emissions testing, it is not unusual to have to move the equipment from two to four times during a test cycle.

Because of the demanding physical nature of current approaches to emissions stack testing, typically two individuals are required to accomplish this testing. In addition, these individuals must have the necessary strength to move heavy equipment, which disqualifies numerous otherwise well qualified individuals from being able to carry out the tasks associated with testing of stack emissions.

Finally, not only is the equipment moved from port to port of an individual stack, industrial facilities which have more than one stack require either the duplication of expensive equipment or the movement of the equipment from one stack to the next in order to test the emissions from more than one stack.

Therefore, a need exists for an improved apparatus for facilitating the testing of emissions from industrial stacks.

SUMMARY OF THE INVENTION

An emissions testing equipment support for use in combination with an elongated emissions sampling probe for monitoring emissions in a stack includes a probe carrier which is adapted for movement on a walkway. The walkway or base provides a convenient work area from which one or more monitoring ports of the stack are accessible. An elongated probe guide is coupled to the probe carrier and an emissions sampling probe is carried by the probe guide for movement along the probe guide toward (into) and away from (out of) the monitoring port. Because of the movable nature of the probe carrier on the walkway, and most preferably the manual movability of this probe carrier with the accompanying emissions testing probe and testing equipment supported thereby, stack emissions testing becomes much easier to accomplish. This is particularly true for stacks having plural monitoring ports because one simply moves the probe carrier and supported equipment on the walkway between ports in order to accomplish sampling of the stack gases at more than one port. In addition, in accordance with the most preferred embodiment of the present invention, the probe guide and emissions stack testing equipment is not connected to the stack and therefore there is no need to disconnect equipment components from the stack to shift the device between ports. Also, this aspect of the invention eliminates the need to mount brackets, chains and the like to the stack for use in supporting stack emissions sampling equipment.

In accordance with another aspect of the present invention, an elevation adjustment mount couples the probe guide to the probe carrier for selectively raising and lowering the probe guide. This elevation adjustment varies the height of the emissions sampling probe relative to a monitoring port to which the probe is to be inserted. Consequently, although the height between a walkway and emissions sampling port may vary from stack to stack, or from port to port, the apparatus of the present invention accommodates these variations with ease. Various mechanisms may be used for adjusting the height of the probe guide, and thereby the probe, relative to the monitoring port. For example, various length-wise adjustable mechanisms may be used to mount the probe guide to the carrier to permit adjustment of the elevation of the probe guide. Turnbuckles and threaded bolts, alone or in combination with one another, are specifically preferred examples. In addition, the probe carrier may include legs of adjustable length for also adjusting the elevation. Telescoping legs and/or removable leg sections are specific examples of this aspect of the invention.

Although various mechanisms may be used to facilitate movement of the probe carrier on the walkway, such as skids, treads, tracks and the like, a specifically preferred approach is to utilize plural wheels for supporting the probe carrier for rolling movement from position to position on the walkway.

As another feature of the present invention, a level indicator, such as a carpenter's level or the like, may be mounted to the probe guide for providing an indication of the positioning of the probe guide in a horizontal plane and the corresponding horizontal positioning of an elongated emissions sampling probe coupled to the probe guide.

As yet another feature of the present invention, an emissions sample support tray may be mounted to the probe carrier for holding emission sample containers, which may be emersed in ice water in the tray.

As yet another specific feature of an illustrated preferred embodiment of the present invention, the probe carrier may comprise first and second spaced apart upright inverted u-shaped end pieces together with plural cross pieces interconnecting the end pieces to provide a rigid probe support frame.

With this construction, the emissions testing equipment may be readily moved from location to location while minimizing the possible disruption of seals between components of the emissions monitoring equipment.

It is accordingly one object of the present invention to provide an improved apparatus for supporting a stack emissions testing probe and related equipment to facilitate monitoring of stack emissions.

The present invention relates to the above features, objects and advantages both individually and collectively. These and other objects, features and advantages of the present invention will become more apparent with reference to the following description and drawings.

DETAILED DESCRIPTION OF A PREFERRED EMBODIMENT

Figure 1:
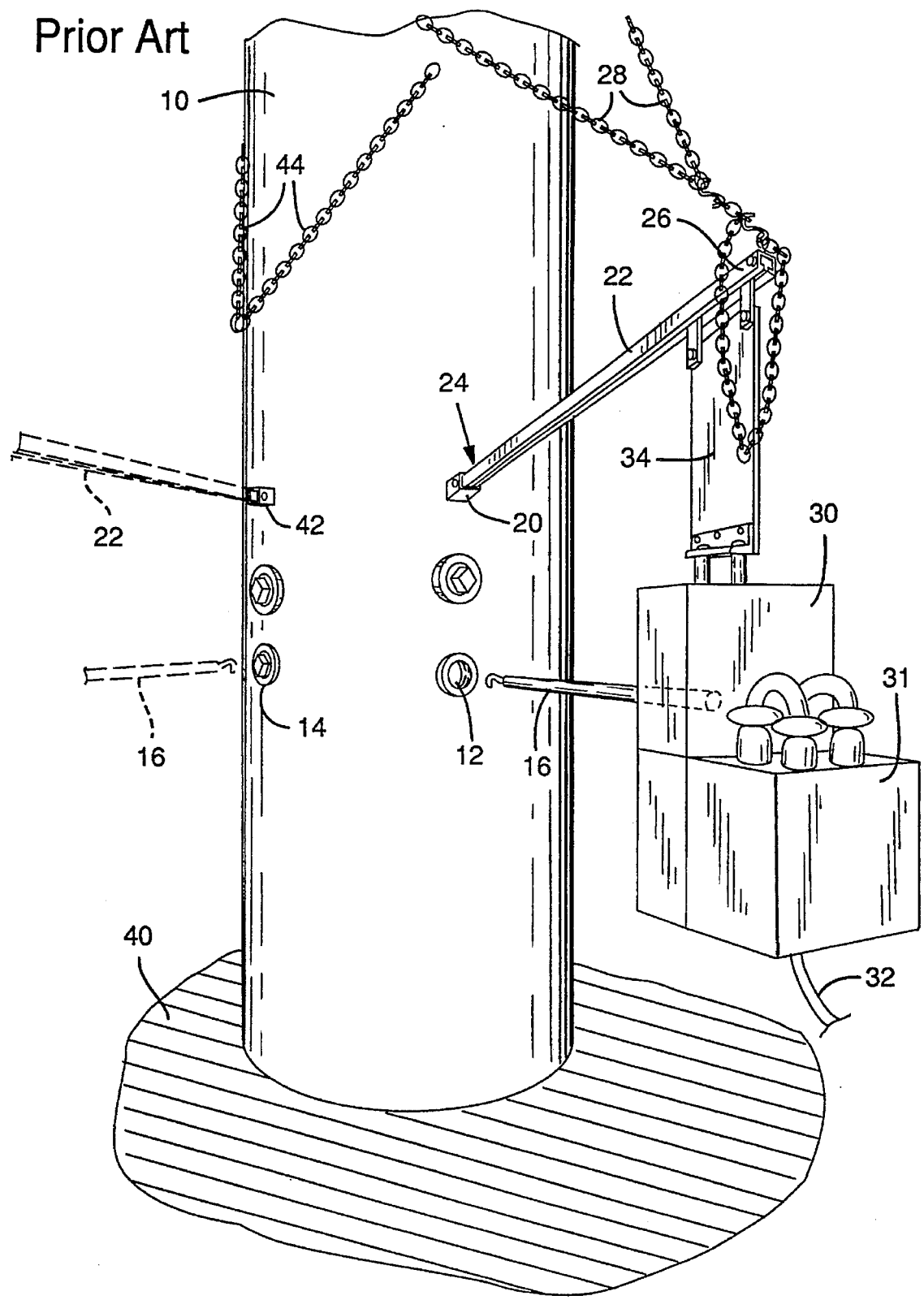
FIG. 1 is a perspective view of prior art stack emissions monitoring equipment.
Figure 2:
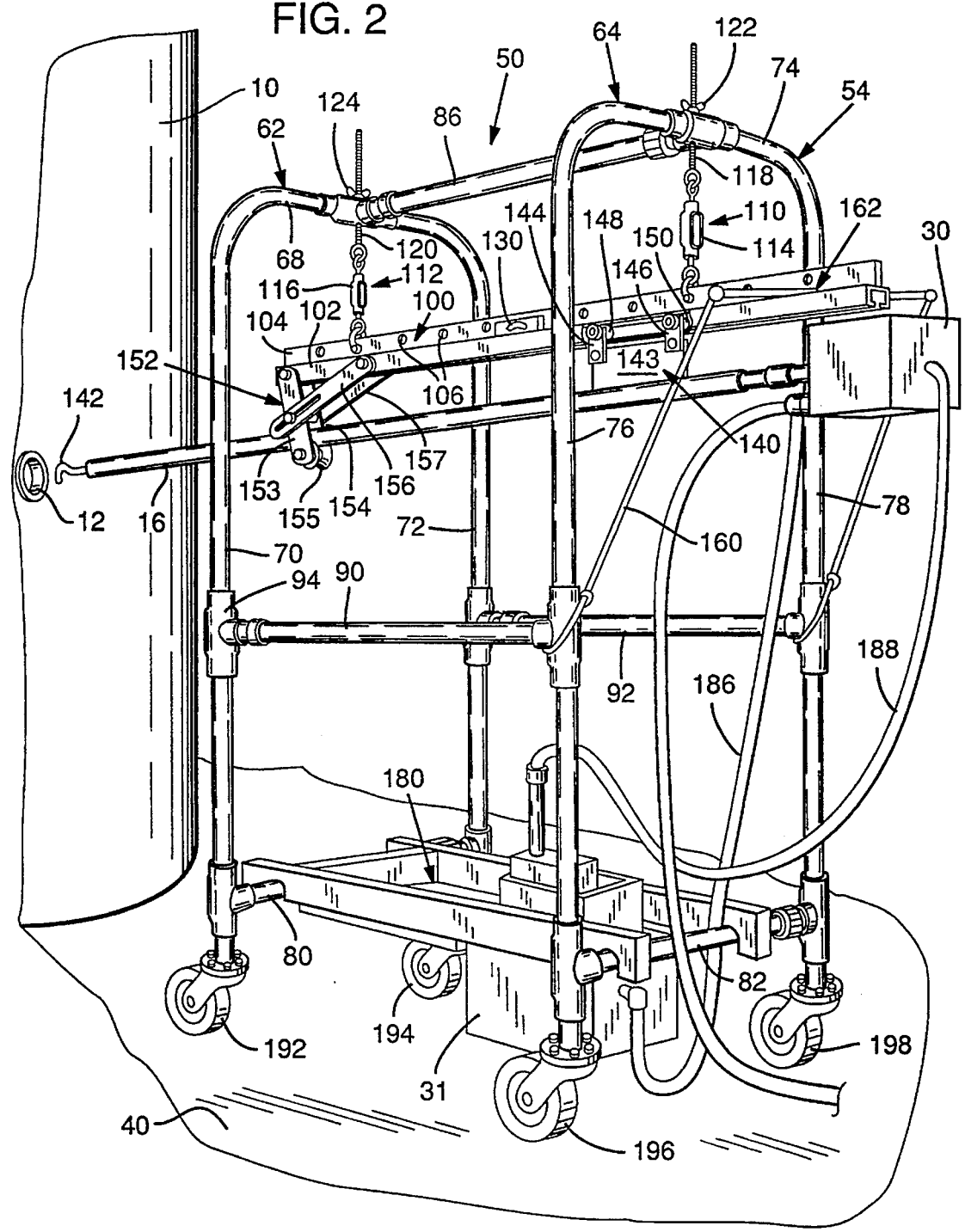
FIG. 2 is a perspective view of an emissions testing equipment support in accordance with the present invention.
Figure 3:
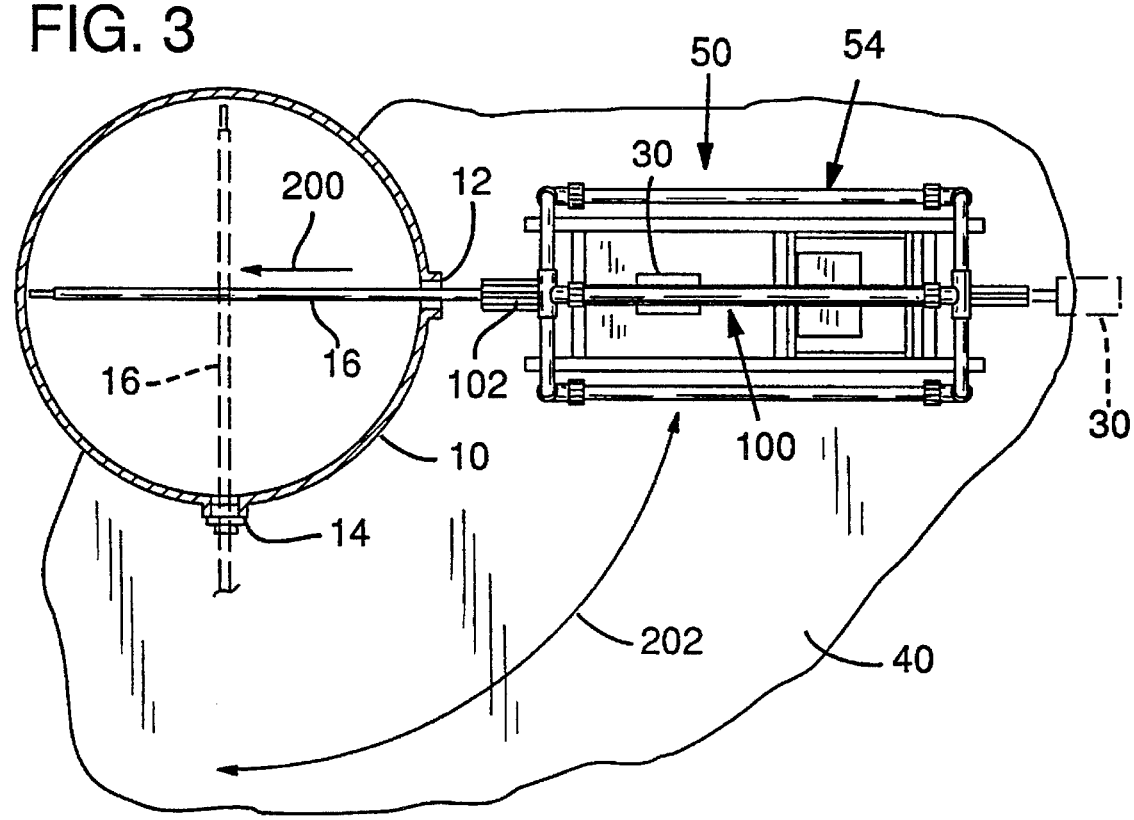
FIG. 3 is a top view of the apparatus of FIG. 2 illustrating in schematic form the shifting of the apparatus between first and second stack monitoring ports.

With reference to FIGS. 2 and 3, a preferred embodiment of an emissions testing equipment support 50 is shown for use in combination with an elongated emissions sampling probe 16 for monitoring emissions in the stack 10. As previously explained, the stack 10 has at least one monitoring port 12, and in this case, as shown in FIG. 3, two such monitoring ports 12, 14 located ninety degrees apart from one another about the periphery of the stack. The emissions sampling probe 16 is inserted through the monitoring ports 12, 14 to obtain emissions samples from within the stack.

The testing equipment support 50 is shown resting on a walkway 40 which provides personnel walking on the walkway with access to the monitoring ports.

The apparatus of the present invention includes a probe carrier, indicated generally at 54, which is adapted for movement on the walkway. Although the probe carrier may take many forms, the illustrated carrier 54 includes first and second inverted u-shaped spaced-apart end pieces 62, 64 which are generally upright, and preferably vertical. The end piece 62 has a transverse or cross section 68 extending between a pair of upright or vertical legs 70, 72. Similarly, the end piece 64 has a cross or transverse section 74 which extends between respective upright or vertical legs 76 and 78. In addition to the upper transverse sections 68, 74, the respective leg pieces also have lower transverse rigidifying pieces 80, 82. Also, to rigidify the structure and provide a rigid frame, an upper longitudinal cross piece 86 extends between the sections 68 and 74. In addition, a first lower longitudinal cross piece 90 extends between legs 70, 76 while a second lower longitudinal cross piece 92 extends between legs 72 and 78. Couplings, such as the one indicated at 94, are used to rigidly interconnect the components forming the frame 54. Although any suitable material may be used for the frame 54, one and one-fourth inch diameter aluminum electrical conduit interconnected with conventional electrical conduit couplings has proven to be suitable.

The frame 54 may of course be constructed of other materials and in other configurations to perform its purpose as a probe carrier for supporting an elongated probe guide, such as indicated at 100 in FIG. 2. However, it is preferable to provide a structure which does not interfere with emissions monitoring equipment as it moves along the probe guide.

The illustrated probe guide 100 includes an inverted elongated channel section 102 with an elongated flange projecting upwardly from the upper surface of the channel. Plural apertures, some being numbered as 106 in FIG. 2, are provided through flange 104 for use in attaching the probe guide 100 to the probe carrier 54. Other equivalent fastening mechanisms, such as hooks welded or otherwise secured to track 102 may of course be used.

The probe guide 100 is suspended from the carrier or frame 54 by a mounting mechanism, such as a pair of mounts 110 and 112. Preferably, the mounts 110, 112 are length-wise adjustable so that they may be adjusted in length to respectively raise or lower the probe guide 100, and thereby the emissions sampling probe 16 to thereby adjust the elevation of the probe 16 to align the probe with a respective monitoring port, such as port 12 shown in FIG. 2. In the illustrated embodiment, each of the mounts 110, 112 include a respective turnbuckle 114, 116 and a respective bolt 118, 120. The bolt 118 passes through the transverse frame element 64 and is held in place by a wing nut 122 threaded onto the bolt. Similarly, the bolt 120 passes through the transverse frame element 68 and is secured in place by a wing nut 124. By turning the wing nuts 122, 124, the bolts 118, 120 are raised and lowered to thereby adjust the elevation of the probe guide 100. In addition, the turnbuckles 114, 116 may likewise be turned to provide additional height or elevation adjustment capabilities.

Preferably the probe guide 100 is adjusted to position the track 102 in a generally horizontal plane. A level indicator, such as a conventional bubble level 130, may be positioned on the probe carrier to provide an indication of the horizontal positioning of the track section 102.

A probe guide coupler 140 is mounted to the probe 16 so as to project upwardly from the probe. Coupler 140 is positioned preferably at the balance point between the emissions sampling equipment 30 at one end of the probe and the probe tip 142 which is to be inserted into the monitoring port. Although not shown in FIG. 2, the bracket 140 may be adjustable along the length of the probe for balancing purposes in the event the equipment package 30 is changed. The specifically illustrated probe guide coupler 140 includes a plate-like bracket 145 with roller carrying legs 144, 146 projecting upwardly therefrom. These legs carry respective rollers 148, 150 which are positioned within and to roll along the guide rail defined by the track section 102. Removable stops, not shown, are positioned at the respective ends of the track section 102 to prevent the rollers from inadvertently leaving the ends of the track.

The probe guide 100 may also include an optional probe end section support 152 (FIG. 2) for assisting in maintaining the probe guide parallel to the rail 102 and thus horizontal when the rail is horizontal. The illustrated support 152 includes a pair of downwardly projecting flanges 153, 154 mounted at their upper ends to respective sides of the rail 102 and supporting a conventional v-shaped roller 155 at their lower ends. The support also includes a pair of angle brace links 156, 157 connected at their respective upper ends to the rail 102. The lower ends of these links are provided with slots (not numbered) through which fasteners extend into the respective flanges 153, 154. These fasteners are tightened after the links 156, 157 are moved to place the flanges and roller in the proper position to hold the probe 16 horizontal. A section of the probe 16 rests on the roller 155 and is thereby supported.

With this construction, the emission sampling equipment 30 and probe 16 may readily be moved along the longitudinal axis of the probe guide 100 for selective insertion of the probe 16 into and removal of the probe from a monitoring port.

An optional tie-down 160, connected to a lower portion of the frame 54 and to the rear end portion 162 of the probe carrier 100 prevents shifting of the rear end of the probe carrier upwardly in the event the equipment package 30 is moved too far forward toward the port. A similar tie-down, not shown, may be positioned at the front end of the probe carrier. Of course, rigid mounts may be used to couple the probe guide 100 to the frame 54, thereby eliminating these optional tie-down elements.

The apparatus may also include an emissions sample supporting tray 180 for supporting emissions sample containers, such as found in a conventional emissions sampling impinger 31, as shown in FIG. 2. These containers are typically placed in ice water. The impinger 31 as well as additional or alternative emissions sampling equipment may be supported by the tray 180 rather than being carried at the end of the probe with the equipment 130. Tools and other equipment may also conveniently be carried on the tray 180. Umbilical hoses or cords, such as indicated at 186 and 188, interconnect the emissions sampling equipment. With this construction, because the apparatus of the present invention supports the bulk of the emissions monitoring equipment, the risk of breaking seals between elements of this equipment is minimized during movement of the emissions monitoring probe 16 and equipment from port to port and from stack to stack.

For purposes of illustration, and not to be construed as a limitation, an exemplary emissions monitoring probe is a Model A-2040 probe available from Research Appliance Company, Division of Anderson Samplers of Atlanta, Ga. Such a probe is connected to conventional emissions monitoring equipment, such as a sample case Model 201010 and other components available from Research Appliance Company, Division of Anderson Samplers. Emissions monitoring equipment of this type has been utilized at many industrial locations, such as in monitoring stack gases at mills owned by Weyerhaeuser Company, the assignee of the present invention.

As previously mentioned, advantageously the support of the present invention is readily movable, and preferably manually portable or movable, to position the probe 16 for insertion into the various monitoring ports of a stack and between stacks. Although the frame 54 may be mounted in any convenient manner for movement on a walkway, such as to skids, rails or on treads, preferably the frame 54 is mounted to wheels to permit rolling of the structure between the ports to be monitored. As illustrated in FIG. 2, a conventional wheel (e.g. 192, 194, 196 and 198) is inserted into the lower end of each of the respective legs 70, 72, 76 and 78 for this purpose.

As specifically illustrated in FIG. 3, to move the emissions sampling probe 16 between ports, the support frame 54 is moved to align the probe with a particular port, such as port 12 in FIG. 3. The probe is then moved along the probe guide 100 and, relative to the frame 54 to insert the probe into the stack 10, as indicated by the arrow 200. Following testing, the probe is removed from port 12 in the direction opposite to direction 200. With the probe removed from the stack 10, the frame 54, and supported probe, is wheeled, as indicated generally by arrow 202, to align the probe 16 with the next port 14. Vertical adjustments of the probe guide is made as required, for example by adjusting mounts 110, 112, to align the probe horizontally and at the same elevation as the monitoring port 14. The probe 16 is then inserted into the port 14 for further stack emissions testing.

As is apparent from the above description, a single individual may readily move the stack emissions monitoring equipment between ports for purposes of accomplishing stack emissions testing without the difficulties encountered in the prior art approach.

Having illustrated and described the principles of my invention with reference to one preferred embodiment, it should be apparent to those of ordinary skill in the art that this invention may be modified in arrangement and detail without departing from such principles. I claim as my invention all such modifications as fall within the scope of the following claims.

I claim:

1. An emissions testing equipment support apparatus for use in combination with an elongated emissions sampling probe for monitoring emissions in a stack, the stack having at least one monitoring port through which the emissions sampling probe may be inserted to obtain emissions samples within the stack, the monitoring port being accessible from a base or walkway, the apparatus comprising:

a probe carrier adapted for movement in contact with the walkway and relative to the walkway;

an elongated probe guide coupled to the probe carrier and movable with the probe carrier as the probe carrier is moved relative to the walkway;

a probe guide coupler hanging down from the probe guide so as to be movable along the length of the probe guide; and an emissions sampling probe carried by the probe guide coupler beneath the probe guide, whereby the emissions sampling probe is movable along the probe guide with the probe guide coupler toward and away from the at least one monitoring port when the probe carrier is in a first position relative to the at least one monitoring port.

2. An apparatus according to claim 1 in which the probe guide coupled is coupled to the emissions sampling probe at a location where the emissions sampling probe is balanced so as to minimize pivoting forces exerted by the emissions sampling probe on the probe guide coupler.

3. An apparatus according to claim 1 in which the probe carrier comprises an upright rack with supporting wheels for rolling the probe carrier in any direction on the walkway.

4. An apparatus according to claim 1 including an elevation adjustment mount positioned to suspend the probe guide from the probe carrier for raising and lowering the probe guide to adjust the elevation of the emissions sampling probe relative to the at least one monitoring port.

5. An apparatus according to claim 3 including an elevation adjustment mount positioned to suspend the probe guide from the probe carrier for raising and lowering the probe guide to adjust the elevation of the emissions sample probe relative to the at least one monitoring port.

6. An apparatus according to claim 5 in which the probe guide has first and second end portions, the elevation adjustment mount comprises first and second turnbuckles coupling respective first and second end portions of the probe guide to the rack.

7. An apparatus according to claim 5 including a horizontal level indicator mounted to the probe guide, the horizontal level indicator providing an indication of the positioning of the probe guide in a horizontal plane.

8. An apparatus according to claim 6 including a horizontal level indicator mounted to the probe guide, the horizontal level indicator providing an indication of the positioning of the probe guide in a horizontal plane.

9. An emissions testing equipment support apparatus for use in combination with an elongated emissions sampling probe for monitoring emissions in a stack, the stack having at least one monitoring port through which the emissions sampling probe may be inserted to obtain emissions samples within the stack, the monitoring port being accessible from a base or walkway, the apparatus comprising:

a probe carrier for positioning on the walkway, the probe carrier being adapted for movement on the walkway;

an elongated probe guide coupled to the probe carrier;

an emissions sampling probe carried by the probe guide for movement along the probe guide toward and away from the at least one monitoring port when the probe carrier is in a first position relative to the at least one monitoring port; and an emissions sample support tray mounted to the probe carrier.

10. An emissions testing equipment support apparatus for use in combination with an elongated emissions sampling probe for monitoring emissions in a stack, the stack having at least one monitoring port through which the emissions sampling probe may be inserted to obtain emissions samples within the stack, the monitoring port being accessible from a base or walkway, the apparatus comprising:

a probe carrier adapted for movement in contact with the walkway and relative to the walkway;

an elongated probe guide coupled to the probe carrier and movable with the probe carrier as the probe carrier is moved relative to the walkway;

a probe guide coupler supported by the probe guide so as to be movable along the length of the probe guide; and an emissions sampling probe carried by the probe guide coupler, whereby the emissions sampling probe is movable along the probe guide with the probe guide coupler toward and away from the at least one monitoring port when the probe carrier is in a first position relative to the at least one monitoring port;

the probe carrier comprising an upright rack with supporting wheels for rolling the probe carrier in any direction on the walkway;

an elevation adjustment mount positioned to suspend the probe guide from the probe carrier for raising and lowering the probe guide to adjust the elevation of the emissions sample probe relative to the at least one monitoring port;

the probe guide having first and second end portions, the elevation adjustment mount comprises first and second turnbuckles coupling respective first and second end portions of the probe guide to the rack;

a level indicator mounted to the probe guide, the level indicator providing an indication of the positioning of the probe guide in a horizontal plane; and an emissions sample support tray mounted to the probe carrier.

11. An apparatus according to claim 1 which includes a probe support mounted to the probe guide for engaging a section of the emissions sampling probe during movement of the emissions sampling probe.

12. An emissions testing equipment support apparatus for use in monitoring emissions in a stack, the stack having plural monitoring ports through which an elongated emissions sampling probe may be inserted to obtain emissions samples at locations within the stack, the monitoring ports being accessible from a base or walkway, the apparatus comprising:

an upright rack movable on the walkway;

a probe guide mounted to an upper portion of the rack, a probe coupler hanging down from and movably mounted to the probe guide and adapted to support an emissions sampling probe beneath the probe guide for movement relative to the rack into and out of the stack monitoring ports;

whereby following the obtaining of emissions samples at one stack monitoring port, the emissions sampling probe may be moved relative to the rack and out of the one stack monitoring port, the upright rack may be moved to position the probe for insertion into another of the stack monitoring ports, and the emissions sampling probe may be moved relative to the rack and into another of the stack monitoring ports.

13. An apparatus according to claim 12 including an elevation adjustment mount which couples the probe guide to the rack for raising and lowering the probe guide to adjust the elevation of the emissions sampling probe relative to the monitoring ports.

14. An apparatus according to claim 13 in which the probe guide has first and second end portions, the elevation adjustment mount comprises first and second turnbuckles coupling respective first and second end portions of the probe guide to the rack.

15. An apparatus according to claim 14 including a level indicator mounted to the probe guide, the level indicator providing an indication of the positioning of the probe guide in a horizontal plane.

16. An emissions testing equipment support apparatus for use in monitoring emissions in a stack, the stack having plural monitoring ports through which an elongated emissions sampling probe may be inserted to obtain emissions samples at locations within the stack, the monitoring ports being accessible from a base or walkway, the apparatus comprising:

an upright rack movable on the walkway;

a probe guide mounted to an upper portion of the rack, a probe coupler movably mounted to the probe guide and adapted to support an emissions sampling probe beneath the probe guide for movement relative to the rack into and out of the stack monitoring ports;

whereby following the obtaining of emissions samples at one stack monitoring port, the emissions sampling probe may be moved relative to the rack and out of the one stack monitoring port, the upright rack may be moved to position the probe for insertion into another of the stack monitoring ports, and the emissions sampling probe may be moved relative to the rack and into another of the stack monitoring ports;

an elevation adjustment mount which couples the probe guide to the rack for raising and lowering the probe guide to adjust the elevation of the emissions sampling probe relative to the one monitoring port;

the probe guide having first and second end portions, the elevation adjustment mount comprising first and second turnbuckles coupling respective first and second end portions of the probe guide to the rack;

a level indicator mounted to the probe guide, the level indicator providing an indication of the positioning of the probe guide in a horizontal plane; and an emissions sample support tray mounted to the rack.

17. An emissions testing equipment support apparatus for use in combination with an elongated emissions sampling probe for monitoring emissions in a stack, the stack having plural monitoring ports through which the emissions sampling probe may be inserted to obtain emissions samples within the stack, the monitoring ports being accessible from a base or walkway, the apparatus comprising:

a probe carrier comprising first and second spaced apart upright inverted u-shaped end pieces and plural cross pieces interconnecting the end pieces to provide a rigid probe support frame, the frame including support wheels rotatably mounted thereto for supporting the frame for rolling on the walkway;

an elongated probe guide rail;

first and second spaced apart adjustable length supports coupling the probe guide rail to an upper section of each end piece for supporting the probe guide rail on the frame in a generally horizontal plane, whereby adjustment of the length of the adjustable length supports varies the elevation of the probe guide rail;

a probe guide coupler movably coupled to the probe guide rail for movement along at least a portion of the length of the probe guide rail; and an elongated emissions probe mounted by the probe guide coupler to the probe guide rail, whereby the elongated emissions probe is movable with the movement of the probe guide coupler into and out of the stack monitoring ports.

18. An apparatus according to claim 17 in which the first and second adjustable length supports each comprise a respective turnbuckle.

19. An apparatus according to claim 17 in which the first and second adjustable length supports each comprise a respective bolt.

20. An apparatus according to claim 17 including an emissions sample support tray mounted to the frame.

21. An apparatus according to claim 17 in which the probe guide coupler includes guide rollers for rolling along the probe guide rail during movement of the probe guide coupler, the probe guide coupler supporting the emissions sampling probe below the guide rollers.

22. An apparatus according to claim 17 including a probe support mounted to the probe guide rail in a position to engage and guide a section of the probe during movement of the probe.

* * * * *